US00PP23286P2

(12) United States Plant Patent
Ault et al.

(10) Patent No.: US PP23,286 P2
(45) Date of Patent: Dec. 25, 2012

(54) ***MONARDA* PLANT NAMED 'FIRE MARSHALL'**

(50) Latin Name: ***Monarda* Hybrid**
Varietal Denomination: Fire Marshall

(75) Inventors: James Robert Ault, Libertyville, IL (US); Catherine S. Thomas, Northfield, IL (US)

(73) Assignee: Chicagoland Grows, Glencoe, IL (US)

( * ) Notice: Subject to any disclaimer, the term of this patent is extended or adjusted under 35 U.S.C. 154(b) by 0 days.

(21) Appl. No.: 13/200,271

(22) Filed: Sep. 22, 2011

(51) Int. Cl.
*A01H 5/00* (2006.01)

(52) U.S. Cl. ..... Plt./455

(58) Field of Classification Search ..... Plt./455
See application file for complete search history.

*Primary Examiner* — Annette Para
(74) *Attorney, Agent, or Firm* — Penny J. Aguirre

(57) ABSTRACT

A new cultivar of bee balm, *Monarda* Hybrid 'Fire Marshall', characterized by its inflorescences that are deep red in color, its clump-forming growth habit, its high level of resistance to powdery mildew, its compact plant habit, its height of about 50 cm, and its hardiness in U.S.D.A. Zones 4 to 7.

2 Drawing Sheets

Botanical classification: *Monarda* Hybrid.

Variety denomination: 'Fire Marshall'.

BACKGROUND OF THE INVENTION

The present invention relates to a new and distinct cultivar of *Monarda* Hybrid. The new cultivar will be referred to hereafter by its cultivar name, 'Fire Marshall'. 'Fire Marshall' is a new variety of bee balm suitable for landscape plantings.

A *Monarda* breeding program was initiated in 2000 in Glencoe, Ill. with the intent of crossing cultivars evaluated by a plant evaluation program that were deemed the most powdery mildew resistant cultivars in the trials. The two parents of 'Fire Marshall', M. 'Marshalls Delight' (not patented) and M. 'Jacob Cline' (not patented), were selected as parents for their attractiveness, higher disease resistance, and overall better plant performance among the plants evaluated during the trials. The goal of crossing these two cultivars was to develop new cultivars of *Monarda* with the same high degree of disease resistance but with novel ornamental traits.

Several flower stems of the seed parent, 'Marshalls Delight' were tied to bamboo garden stakes just prior to Jun. 27, 2000. This was done to stabilize the stems so they would not break during subsequent flower manipulation and pollination. The terminal inflorescence of each tied-up stem was then enclosed in an insect-barrier pollination bag. As *Monarda* plants are self-compatible, individual flowers were emasculated the day before anthesis by prying open the corolla tube and removing the nondehisced anthers. Pollen from 'Jacob Cline' was then applied the following day to the style of each emasculated flower. A total of 17 seeds were produced from the above cross, germinated the spring of 2001, and placed in the research garden that same year. The new cultivar, 'Fire Marshall', was selected in summer of 2006 as a single unique plant from the above cross.

The new cultivar was first asexually propagated by shoot tip cuttings by one of the Inventors in Glencoe, Ill. in May of 2007. Asexual propagation has determined that the characteristics of this cultivar are stable and are reproduced true to type in successive generations.

SUMMARY OF THE INVENTION

The following traits have been repeatedly observed and represent the characteristics of the new *Monarda*. These attributes in combination distinguish 'Fire Marshall' as a unique cultivar of *Monarda*.

1. 'Fire Marshall' exhibits inflorescences that are deep red in color.
2. 'Fire Marshall' exhibits a clump-forming growth habit, rather than the aggressively spreading growth habit that is observed with many cultivars of *Monarda*.
3. 'Fire Marshall' has shown a high level of resistance to powdery mildew (*Sphaerotheca pannosa* var. *rosa*) under the conditions tested.
4. 'Fire Marshall' reaches a height of about 50 cm.
5. 'Fire Marshall' exhibits a compact plant habit relative to its parent plants and many cultivars of *Monarda*.
6. 'Fire Marshall' is hardy in U.S.D.A. Zones 4 to 7.

The new cultivar of *Monarda* can be readily distinguished from other cultivars. The parent plants of 'Fire Marshall', 'Marshalls Delight' and 'Jacob Cline' are the closest comparison cultivars known to the Inventors. 'Marshalls Delight' is similar to 'Fire Marshall' in bloom period and in having a clump-forming growth habit, however 'Marshalls Delight' differs from 'Fire Marshall' in being taller in height (about 71 cm) and in having inflorescences that are purple-pink in color. 'Jacob Cline' is similar to 'Fire Marshall' in blooming period and in having inflorescences that are red in color. 'Jacob Cline' differs from 'Fire Marshall' in being taller in height, in having larger inflorescences, and in having a more spreading growth habit. 'Fire Marshall' can also be compared to 'Cambridge Scarlet' (not patented), which is similar to 'Fire Marshall' in having inflorescences that are red in color and blooming more or less the same time period. 'Cambridge Scarlet' differs from 'Fire Marshall' in being taller in height (96 cm), exhibiting poor powdery mildew resistance, and exhibiting some winter hardiness damage under the testing conditions.

BRIEF DESCRIPTION OF THE DRAWING

The accompanying colored photographs illustrate the overall appearance and distinct characteristics of five year-old plants of the new *Monarda* as grown outdoors in a trial plot in Glencoe, Ill.

DETAILED BOTANICAL DESCRIPTION

Figure 1:
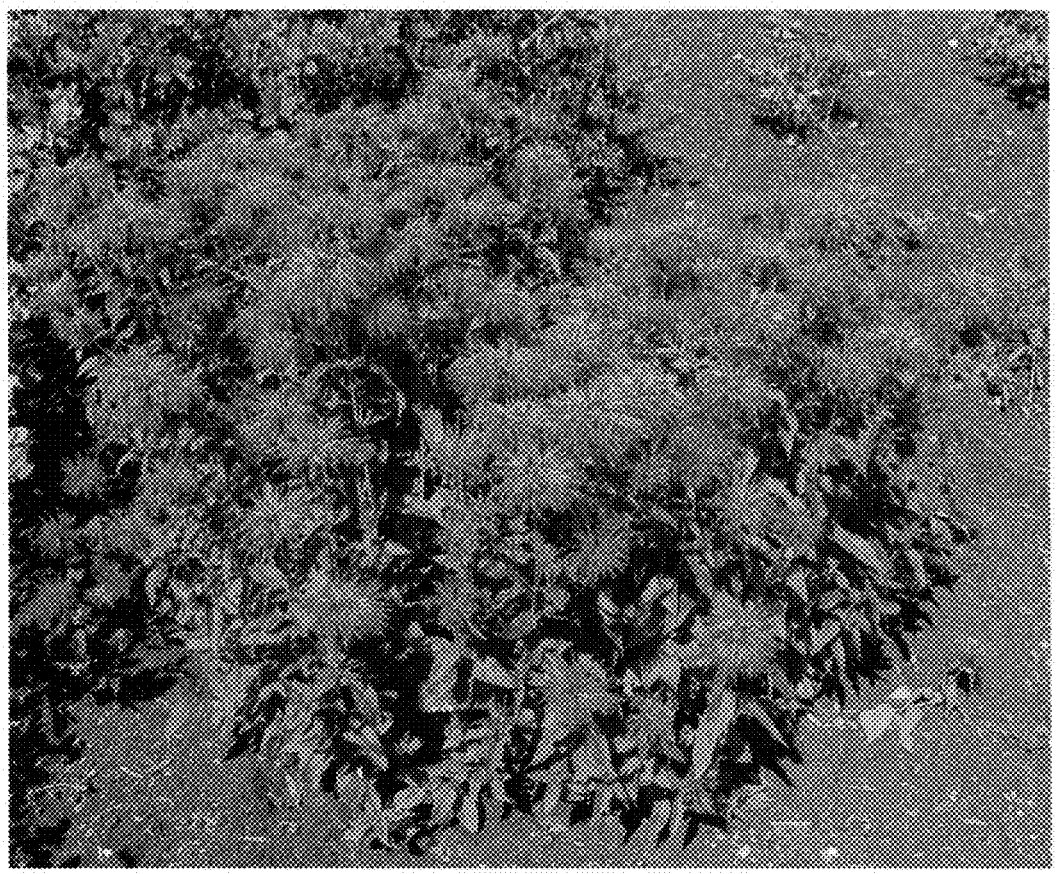
FIG. 1 provides a view of the plant habit of 'Fire Marshall' in bloom.
Figure 2:
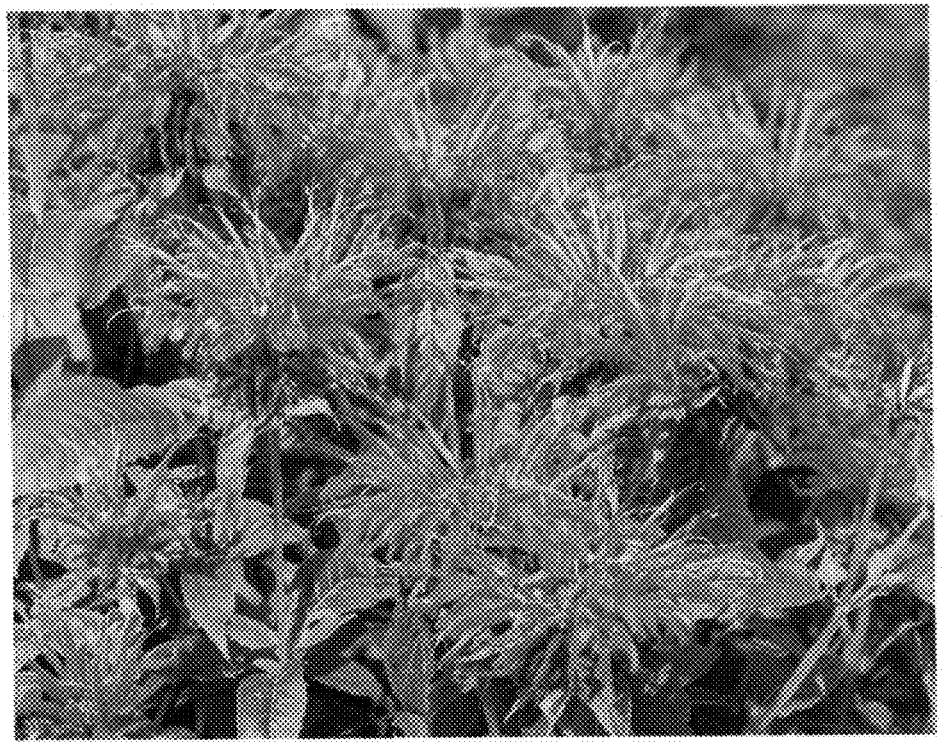
FIG. 2 provides a view of inflorescences of 'Fire Marshall'.
Figure 3:
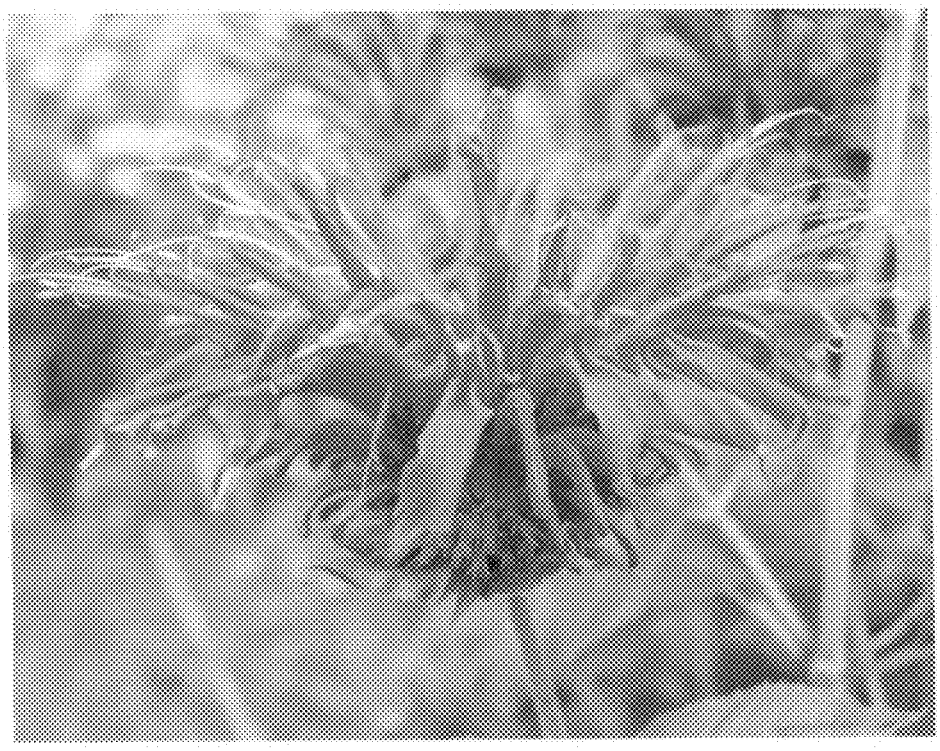
FIG. 3 provides a close-up view of an inflorescence of 'Fire Marshall'. The colors in the photographs are as close as possible with digital photography techniques available, the color values cited in the detailed botanical description accurately describe the colors of the *Monarda*.

The following is a detailed description of two-year old plants of the new cultivar as grown outdoors in a garden in New Hope, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—6 to 8 weeks, from mid to late June to early August in Illinois.

*Plant habit.*—Compact and clump-forming with upright stems, less spreading than is typical of most *Monarda* cultivars.

*Height and spread.*—Reaches about 50 cm in height and 55 cm in spread.

*Hardiness.*—U.S.D.A. Zones 4 to 7.

*Diseases.*—A high degree of resistance was observed to powdery mildew (*Sphaerotheca pannosa* var. *rosa*) in northern Illinois.

*Propagation.*—Shoot tip cuttings approximately 4 inches long taken from actively growing shoots, the basal end of each shoot are treated with a five second dip of 1,250 ppm K-IBA, stuck in 2½" pots (SVD2.5) containing a growing medium of 2 parts perlite to 1 part peat (by volume), and placed in a fog house with bottom heat of 75° F. and air temperature of 70° to 80° F., rooting occurs in 4 weeks.

*Growth rate.*—Moderate for a *Monarda* cultivar.

Stem description:

*Stem shape.*—Square.

*Stem color.*—Young; 137C and 144C, mature wood; blend of 147A and 199A with highlights of 200C, particularly around nodes.

*Stem surface.*—Pubescent when young, becomes woody as it matures.

*Lateral branches.*—Average of 6 per 35 cm stem, average of 8.1 cm in length in the middle of branch and 62 cm in length on the top 12 cm of the stem, average of 3 cm in diameter, internode length of 2.8 to 7.5 cm.

Foliage description:

*Leaves.*—Opposite arrangement, ovate-lanceolate in shape, rounded base, acuminate apex, serrulate margins, slightly glossy on upper surface and lower surface, average of 6.5 cm in length and 3.2 cm in width, color: young foliage upper surface; 137A, young foliage lower surface; color between 137C and 138B, mature foliage upper surface; 137A, mature foliage lower surface; a color between 137B and 137C, venation pinnate with mid-rib on upper surface maturing to 159B in color.

*Petioles.*—Average of 1.5 cm in length and 3 mm in diameter, color of upper surface and lower surface 144A with 59A towards base, pubescent surface.

Inflorescence description:

*Inflorescence type.*—Borne terminally in whorls or as verticillaster.

*Inflorescence number.*—1 per lateral stem.

*Inflorescence fragrance.*—Pungent mint.

*Inflorescence size.*—Average of 5 cm in depth and 4.5 cm in diameter.

*Peduncles.*—Average of 2.5 cm in length and 3.4 mm in diameter, surface is glabrous with pubescence on edges, color is 137B with highlights of 138B on edges.

*Bracts.*—About 30 per verticillaster, smaller bracts linear in shape, 0.5 to 1 cm in length, 1 to 3 mm in width, larger bracts lanceolate in shape average of 4.2 cm in length and 2.1 cm in width, margins ciliate, lower surface densely pubescent, upper surface sparsely pubescent, color of upper surface is 137B with 184C towards midvein and 183B towards apex, color of lower surface is between 137C and 137D with 183A towards apex.

*Floret buds.*—Elongated tube in shape and recurved on upper portion, average of 2.8 cm in length and 3 mm in width prior to opening, 53A in color, surface is pubescent with hairs 53A in color.

*Floret longevity.*—About 5 to 7 days, depending on temperature (on the plant).

*Floret type.*—Tubular.

*Floret quantity.*—Average of 60 per verticillaster.

*Floret size.*—Average of 8 mm in diameter and 4.5 cm in depth.

*Sepals.*—5 per verticillaster, calyx tubular, average of 1.0 cm in length and 5 mm in width, sepals fused except for acuminate apex 3 mm in length, margin entire, upper surface and lower surface glabrous, color of upper surface on opening florets; 144A suffused with 183B near apex, color of lower surface on opening florets; 144B suffused with 183B near apex and margin, fully open florets upper surface; color between 144A to 144B suffused with 183B near apex, base and on main vein, fully open florets lower surface; 144B suffused with 183B on apex and margin.

*Petals.*—5 petals 53B to 53D in color; 2 fused petals forming upper lip; linear in shape, held upright, about 1.3 cm in length and 2 mm in width, acuminate apex, 3 fused petals forming lower lip; somewhat curled, diamond-shaped, with a mucronate apex, held at a 45° to upper lip, average of 12 cm in length and 6 mm in width, both lips; upper surface glabrous, lower surface pubescent with hairs 53D in color, entire margins, base fused to tube; 1.2 cm in length and 2 mm in width, 53D in color with pubescent surface.

*Pistils.*—1, stigma 2 mm in length and 0.5 mm in width, 47B in color, style 3.8 cm in length and 48C in color, ovary minute.

*Stamens.*—2 per floret, filaments 1.7 cm in length, 48C in color, anthers 2 mm in length, 1 mm in width and 200A in color, pollen abundant and 21A in color.

*Seeds.*—1 per floret, average of 0.7 mm in length and 0.4 mm in diameter, oval to rice-shaped, color is 199C.

It is claimed:

1. A new and distinct cultivar of *Monarda* plant named 'Fire Marshall' as herein illustrated and described.

* * * * *